United States Patent
Van Der Beek et al.

(10) Patent No.: US 9,649,286 B2
(45) Date of Patent: *May 16, 2017

(54) METABOLIC IMPRINTING EFFECTS OF SPECIFICALLY DESIGNED LIPID COMPONENT

(71) Applicant: N.V. Nutricia, Zoetermeer (NL)

(72) Inventors: Eline Marleen Van Der Beek, Utrecht (NL); Marieke Abrahamse-Berkeveld, Utrecht (NL); Annemarie Oosting, Utrecht (NL); Martine Sandra Alles, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/954,370

(22) Filed: Nov. 30, 2015

(65) Prior Publication Data

US 2016/0081963 A1 Mar. 24, 2016

Related U.S. Application Data

(62) Division of application No. 14/126,398, filed as application No. PCT/NL2012/050427 on Jun. 18, 2012, now Pat. No. 9,532,966.

(30) Foreign Application Priority Data

Jun. 16, 2011 (WO) ................ PCT/NL2011/050437

(51) Int. Cl.
| | | |
|---|---|---|
| *A61K 38/00* | (2006.01) | |
| *A61K 31/202* | (2006.01) | |
| *A61K 31/201* | (2006.01) | |
| *A61K 31/20* | (2006.01) | |
| *A61K 31/70* | (2006.01) | |
| *A61K 38/02* | (2006.01) | |
| *A61K 31/7016* | (2006.01) | |
| *A61K 35/20* | (2006.01) | |
| *A23L 33/00* | (2016.01) | |
| *A23L 33/115* | (2016.01) | |
| *A23L 33/12* | (2016.01) | |
| *A23L 35/00* | (2016.01) | |

(52) U.S. Cl.
CPC .......... *A61K 31/202* (2013.01); *A23L 33/115* (2016.08); *A23L 33/12* (2016.08); *A23L 33/30* (2016.08); *A23L 33/40* (2016.08); *A23L 35/10* (2016.08); *A61K 31/20* (2013.01); *A61K 31/201* (2013.01); *A61K 31/70* (2013.01); *A61K 31/7016* (2013.01); *A61K 35/20* (2013.01); *A61K 38/02* (2013.01); *A23V 2002/00* (2013.01)

(58) Field of Classification Search
None
See application file for complete search history.

(56) References Cited

U.S. PATENT DOCUMENTS

2008/0058415 A1 3/2008 Shulman et al.

FOREIGN PATENT DOCUMENTS

| FR | 2930406 A1 | 10/2009 |
|---|---|---|
| WO | WO-2005/051091 A1 | 6/2005 |
| WO | WO-2007/073192 A2 | 6/2007 |
| WO | WO-2007/073193 A2 | 6/2007 |
| WO | WO-2010/027258 A1 | 3/2010 |
| WO | WO-2010/027259 A1 | 3/2010 |
| WO | WO-2010/068103 A1 | 6/2010 |
| WO | WO-2010/068105 A1 | 6/2010 |

OTHER PUBLICATIONS

Translation of EP2389076, Lhelias, Oct. 2009, which is the equivalent of EP2389077, accessed at http://www.google.com/patents/EP2389076B1?cl=zh.
Translation of W02005051091, Shulan, Jun. 2005, acessed at https://www.google.com/patents/W02005051091A1 ?cl=en&dq=wo2005051091&hl=en&sa=X&ved=OahUKEwjdOututTJAhWko4MKHT3nAlgQ6AEIHTAA.
International Search Report of PCT/NL2012/050427 dated Oct. 1, 2012.
International Search Report of PCT/NL2012/050428 dated Oct. 1, 2012.

*Primary Examiner* — Jeanette Lieb
(74) *Attorney, Agent, or Firm* — Gilberto M. Villacorta; Sunit Talapatra; Foley & Lardner LLP

(57) ABSTRACT

The invention relates to the use of specifically designed lipid component with optimal fatty acid profile, an enhanced portion of the palmitic acid residues in the sn-2 position and present as lipid globules with a phospholipid coating for an early in life diet for improving the development of a healthy body composition, in particular prevention of obesity, later in life.

17 Claims, No Drawings

METABOLIC IMPRINTING EFFECTS OF SPECIFICALLY DESIGNED LIPID COMPONENT

CROSS-REFERENCE TO RELATED APPLICATIONS

This application is a Divisional application of U.S. patent application Ser. No. 14/126,398, filed as the National Phase Application of International Patent Application No. PCT/NL2012/050427, filed Jun. 18, 2012, published on Dec. 20, 2012, as WO 2012/173485, which claims priority to International Application No. PCT/NL2011/050437, filed Jun. 16, 2011. The contents of these applications are herein incorporated by reference in their entirety.

FIELD OF THE INVENTION

The present invention relates to the field of infant nutrition and the effect of the lipid component of the early in life diet on the health and body composition later in life.

BACKGROUND OF THE INVENTION

Breast-feeding is the preferred method of feeding infants. Breast fed infants have a decreased chance of becoming obese later in life, compared to standard formula fed infants, but little is known about the effects of ingredients in the infant formulae on obesity later in life. Obesity is a major health problem in the Western world. It is a medical condition in which excess fat has accumulated to the extent that it may have an adverse effect on health, leading to reduced life expectancy and it is associated with many diseases, particularly heart disease and type 2 diabetes. Obesity is a leading preventable cause of death worldwide, with increasing prevalence in adults and children, and authorities view it as one of the most serious public health problems of the $21^{st}$ century.

Infant nutrition with a lipid component preventing obesity later in life are known. WO 2007/073192 relates to infant formulae comprising a low amount of linoleic acid and a low weight ratio of linoleic acid to alpha-linolenic acid and LC-PUFA for the prevention of obesity later in life. WO 2007/073193 relates to infant formulae with specific linoleic acid to alpha-linolenic acid ratio's, low linoleic acid content and comprising phospholipids, sphingolipids, cholesterol and/or choline plus uridine for the prevention of obesity later in life.

The lipid component in infant formulae typically is present in the form of small lipid globules, which are obtained after a severe homogenization step. Small lipid globules are desired because it results in a stable, non creaming, emulsion of lipid globules. The globules have a large surface area and because of the low amount of polar lipids, such as phospholipids, in the vegetable oils, the surface of the lipid globules is coated mainly with proteins, typically casein.

WO 2010/0027258 and WO 2010/0027259 relate to infant formulae with large lipid globules coated with phospholipids for the prevention of obesity later in life.

Infant formulae comprise predominantly vegetable oils as lipid source and in vegetable oils, unlike in human or bovine milk fat, the palmitic acid is mainly located at the sn-1 and sn-3 position of the triglyceride molecule. The pancreatic lipases specifically hydrolyse the palmitic acid and the liberated free palmitic acid easily forms calcium-fatty acid complexes in the intestine, thereby reducing the bioavailability of calcium and palmitic acid and increasing stool hardness.

Synthetic or structured lipids are known in the art which comprise more palmitic acid residues in the sn-2 position and their presence in infant formulae increases palmitic acid absorption, calcium absorption and softness of stools. Also an increase in bone mass is reported. Reduction of obesity later in life has never been disclosed.

WO 2005/051091 discloses a lipid preparation, to be included in infant formulae as a beneficial ingredient per se and for improving cognitive and vision development in particular, that is organised in a globular microstructure naturally occurring in human milk that is based on vegetal lipids and a combination of the glycerophospholipids phosphatidylcholine (PC), phosphatidylethanolamine (PE), phosphatidylserine (PS) and phosphatidylinositol (PI), and structured triglycerides such as Betapol® or InFat™. The lipid preparation further can be enriched with omega-3 and omega-6 fatty acids, especially DHA and ARA.

WO 2010/068105 discloses nutritional compositions for infants with a large lipid globule size. The present invention aims to provide infant nutrition with a lipid component beneficially effecting health and/or the body composition later in life.

SUMMARY OF THE INVENTION

The inventors surprisingly found that administration early in life of a diet comprising a lipid component with triglycerides with an increased portion of the palmitic acid residues esterified on the sn-2 position of the glycerol backbone, affects the growth and body composition later in life. When early in life a diet of the present invention that comprised triglycerides with increased palmitic acid residues esterified on the sn-2 position had been administered, it was observed that later in life the body composition was changed, resulting in less fat mass accumulation, less fat mass relative to total body weight, increased lean body mass, increased body weight and increased muscle tissue compared to the body composition upon administering early in life a control diet with conventional, vegetable, triglycerides, even when the diet consumed later in life was the same in both groups. This decreased fat mass accumulation was observed, even when total body weight accumulation was increased. In particular the visceral adipose tissue relative to subcutaneous adipose tissue was reduced. This is surprising, since triglycerides with palmitic acid at the sn-2 position of the triglyceride backbone increase the absorption of fat, i.e. palmitic acid. Visceral obesity is most associated with health problems.

The inventors recognized that when the lipid component is further adapted in its macromolecular architecture by being organized in lipid globules, which are coated with phospholipids, preferably phospholipids derived from milk, the programming effect on body composition and/or health effects later in life, in particular regarding obesity and insulin resistance and diabetes mellitus type 2, is advantageously further improved. It was recognized that an even further improvement can be achieved by optimizing the fatty acid composition. In particular the inventors further recognized that the presence of triglycerides with increased palmitic acid residues esterified on the sn-2 position instead of the sn-1 or sn-3 positions in combination with an optimal fatty acid profile, preferably an optimal fatty acid profile with respect to the weight ratio of linoleic acid to alpha-linolenic can result in an even further improvement of the programming effect on body composition and/or health effects, in particular regarding obesity and insulin resistance and diabetes mellitus type 2, later in life.

This effect later in life is different from the direct effect on the diet. At the end of dietary intervention at day 42, a similar fat mass relative to total body weight, is observed compared to the control diet. Fat mass in young children has important roles in energy storage, insulation, storage of fat soluble vitamins and hormonal development, such as the development of leptin and insulin sensitivity and it is therefore not desired to decrease fat mass in infants and young children. So due to the lipids of the present invention consumed in infancy differences in patterns of growth arise and the body is programmed differently which results in a healthier body composition later in life, i.e. adulthood. The body is programmed to resist a relatively obesogenic Western style diet.

The present invention hence relates to nutritional compositions, in particular formulae for infants or growing up milks for toddlers, comprising a lipid component with a structural design specifically adapted on multiple levels, level one being an improved fatty acid composition with optimal low n6/n3, in particular linoleic acid/alpha-linolenic acid ratio's, level two being an increased number of palmitic acid residues located at the sn-2 position on the triglyceride backbone and level three being the presence of a phospholipid coating on the surface of the lipid globule. The present invention therefore can be used for food compositions intended for infants and/or toddlers and preferably is intended to be consumed early in life in order to prevent obesity, visceral obesity, decrease or prevent insulin resistance, prevent diabetes type 2, prevent metabolic syndrome, cardio- or cerebrovascular diseases, increase lean body mass, increase muscle tissue, decrease relative fat mass, decrease fat mass accumulation, increase bone mass and/or increase bone mineral density later in life.

DETAILED DESCRIPTION OF THE INVENTION

The invention thus concerns a nutritional composition comprising carbohydrates, protein and lipid, wherein the lipid is present in the form of lipid globules, wherein
i) the fatty acid composition of the lipid comprises linoleic acid and alpha-linolenic acid in a weight ratio of 2 to 10,
ii) the fatty acid composition of the lipid comprises at least 10 wt. % palmitic acid based on total fatty acids, and at least 15 wt. % of this palmitic acid is esterified to the sn-2 position of a triglyceride based on total palmitic acid,
iii) the lipid globules are at least partly coated on the surface with phospholipids, the amount of phospholipids present in the nutritional composition being from 0.5 to 20 wt. % phospholipids based on total lipid,
wherein the nutritional composition is not human milk.

The invention also concerns a nutritional composition as defined herein, for use in one or more selected from prevention of obesity, reducing the risk of obesity, treatment of obesity, prevention of diabetes type 2, reducing the risk of occurrence of insulin resistance and improving insulin sensitivity, preventing metabolic syndrome and preventing of osteopenia and/or osteoporosis, reducing the risk of occurrence of osteopenia and/or osteoporosis.

The invention also concerns a nutritional composition as defined herein, for use in improving body composition, the improvement of body composition being selected from the group consisting of increased lean body mass, decreased fat mass relative to total body weight, decreased visceral fat mass relative to total body weight, decreased visceral fat mass relative to total fat mass, decreased fat accumulation and increased muscle mass and increased bone mass and increased bone mineral density.

The invention also concerns a method for one or more selected from prevention of obesity, reducing the risk of obesity, treatment of obesity, prevention of diabetes type 2, reducing the risk of occurrence of insulin resistance and improving insulin sensitivity, preventing or reducing the risk of occurrence of metabolic syndrome, preventing or reducing the risk of occurrence of osteopenia or osteoporosis, comprising administering a nutritional composition comprising carbohydrates, protein and lipid, wherein the lipid is present in the form of lipid globules, wherein
i) the fatty acid composition of the lipid comprises linoleic acid and alpha-linolenic acid in a weight ratio of 2 to 10,
ii) the fatty acid composition of the lipid comprises at least 10 wt. % palmitic acid based on total fatty acids, and at least 15 wt. % of this palmitic acid is esterified to the sn-2 position of a triglyceride based on total palmitic acid,
iii) the lipid globules are at least partly coated on the surface with phospholipids, the amount of phospholipids present in the nutritional composition being from 0.5 to 20 wt. % phospholipids based on total lipid,
and wherein the nutritional composition is not human milk.

In other words the invention concerns the use of a composition comprising carbohydrates, protein and lipid, wherein the lipid is present in the form of lipid globules, wherein
i) the fatty acid composition of the lipid comprises linoleic acid and alpha-linolenic acid in a weight ratio of 2 to 10,
ii) the fatty acid composition of the lipid comprises at least 10 wt. % palmitic acid based on total fatty acids, and at least 15 wt. % of this palmitic acid is esterified to the sn-2 position of a triglyceride based on total palmitic acid,
iii) the lipid globules are at least partly coated on the surface with phospholipids, the amount of phospholipids present in the nutritional composition being from 0.5 to 20 wt. % phospholipids based on total lipid,
and wherein the nutritional composition is not human milk, for the manufacture of a nutritional composition for use in one or more selected from prevention of obesity, reducing the risk of obesity, treatment of obesity, prevention of diabetes type 2, reducing the risk of occurrence of insulin resistance, preventing metabolic syndrome and improving insulin sensitivity, and preventing of osteoporosis or osteopenia.

The invention also concerns a method for improving body composition, preferably a non-therapeutic method for improving body composition, the improvement of body composition being selected from the group consisting of increased lean body mass, decreased fat mass relative to total body weight, decreased visceral fat mass relative to total body weight, decreased visceral fat mass relative to total fat mass, decreased fat accumulation, increased muscle mass, increased bone mass, and increased bone mineral density, comprising administering a nutritional composition comprising carbohydrates, protein and lipid, wherein the lipid is present in the form of lipid globules, wherein
i) the fatty acid composition of the lipid comprises linoleic acid and alpha-linolenic acid in a weight ratio of 2 to 10,
ii) the fatty acid composition of the lipid comprises at least 10 wt. % palmitic acid based on total fatty acids, and at least 15 wt. % of this palmitic acid is esterified to the sn-2 position of a triglyceride based on total palmitic acid,
iii) the lipid globules are at least partly coated on the surface with phospholipids, the amount of phospholipids present in the nutritional composition being from 0.5 to 20 wt. % phospholipids based on total lipid, and wherein the nutritional composition is not human milk.

In other words the invention concerns the use of a composition comprising carbohydrates, protein and lipid, wherein the lipid is present in the form of lipid globules, wherein i) the fatty acid composition of the lipid comprises linoleic acid and alpha-linolenic acid in a weight ratio of 2 to 10, ii) the fatty acid composition of the lipid comprises at least 10 wt. % palmitic acid based on total fatty acids, and at least 15 wt. % of this palmitic acid is esterified to the sn-2 position of a triglyceride based on total palmitic acid, iii) the lipid globules are at least partly coated on the surface with phospholipids, the amount of phospholipids present in the nutritional composition being from 0.5 to 20 wt. % phospholipids based on total lipid, and wherein the nutritional composition is not human milk, for the manufacture of a nutritional composition for use in improving body composition, the improvement of body composition being selected from the group consisting of increased lean body mass, decreased fat mass relative to total body weight, decreased visceral fat mass relative to total body weight, decreased visceral fat mass relative to total fat mass, decreased fat accumulation, increased muscle mass, increased bone mass and increased bone mineral density.

Obesity is considered to be a medical condition and thus prevention of obesity, reducing the risk of obesity, and/or treatment of obesity is seen as a method of treatment of the human body by therapy. This includes visceral obesity. Human subjects may suffer from visceral obesity, but not from overall obesity. This situation is described as thin on the outside, fat on the inside, which is abbreviated in the art as TOFI. A person suffering from visceral obesity is more at risk of becoming diabetic, even though overall obesity is not present. Thus visceral obesity is considered to be a medical condition as well and thus prevention of visceral obesity, reducing the risk of visceral obesity, and/or treatment of visceral obesity is seen as a method of treatment of the human body by therapy. However, improving body composition can be considered as not being therapeutic meaning that for all jurisdictions this aspect can be properly worded by the method, more in particular a non-therapeutic method, for improving body composition as specified above.

Diabetes mellitus type 2, also referred to as diabetes type 2, is considered to be a medical condition and thus prevention of diabetes type 2, reducing the risk of diabetes type 2, and/or treatment of diabetes type 2 is seen as a method of the human body by therapy. Likewise, decreasing insulin resistance, or the preventing occurrence of insulin resistance, or improving insulin sensitivity, is seen as a medical treatment.

Lipid Component

The composition that is to be administered according to the present method or use comprises lipids. Lipids in the present invention are one or more selected from the group consisting of triglycerides, polar lipids (such as phospholipids, cholesterol, glycolipids, sphingomyelin), free fatty acids, mono- and diglycerides. Preferably the composition comprises at least 70 wt. %, more preferably at least 80 wt. %, more preferably at least 85 wt. % triglycerides, even more preferably at least 90 wt % triglycerides based on total lipids.

The lipid provides preferably 30 to 60% of the total calories of the composition. More preferably the present composition comprises lipid providing 35 to 55% of the total calories, even more preferably the present composition comprises lipid providing 40 to 50% of the total calories. When in liquid form, e.g. as a ready-to-feed liquid, the composition preferably comprises 2.1 to 6.5 g lipid per 100 ml, more preferably 3.0 to 4.0 g per 100 ml. Based on dry weight the present composition preferably comprises 10 to 50 wt. %, more preferably 12.5 to 40 wt. % lipid, even more preferably 19 to 30 wt. % lipid. The lipid comprises preferably from 80 to 100 wt. % triglycerides based on total lipid, more preferably 90 to 100 wt. %.

The lipid of the present invention preferably comprises vegetable lipids. The presence of vegetable lipids advantageously enables an optimal fatty acid profile, high in (poly) unsaturated fatty acids and/or more reminiscent to human milk fat. Using lipids from cow's milk alone, or other domestic mammals, does not provide an optimal fatty acid profile. This less optimal fatty acid profile, such as a large amount of saturated fatty acids, is known to result in increased obesity. Preferably the present composition comprises at least one, preferably at least two lipid sources selected from the group consisting of linseed oil (flaxseed oil), rape seed oil (such as colza oil, low erucic acid rape seed oil and canola oil), *salvia* oil, *perilla* oil, purslane oil, lingonberry oil, sea buckthorn oil, hemp oil, sunflower oil, high oleic sunflower oil, safflower oil, high oleic safflower oil, olive oil, black currant seed oil, echium oil, coconut oil, palm oil and palm kernel oil. Preferably the present composition comprises at least one, preferably at least two lipid sources selected from the group consisting of linseed oil, canola oil, coconut oil, sunflower oil and high oleic sunflower oil. When in liquid form, e.g. as a ready-to-feed liquid, the composition preferably comprises 2.1 to 6.5 g vegetable lipid per 100 ml, more preferably 3.0 to 4.0 g per 100 ml. Based on dry weight the present composition preferably comprises 10 to 50 wt. %, more preferably 12.5 to 40 wt. % vegetable lipid, even more preferably 19 to 30 wt. %. Preferably the composition comprises 40 to 100 wt. % vegetable lipids based on total lipids, more preferably 50 to 100 wt. %, more preferably 70 to 100 wt. %, even more preferably 75 to 97 wt. %. It is noted therefore that the present composition also may comprise non-vegetable lipids. Non-vegetable lipids may include milk fat, milk derived lipids as a preferred source of phospholipids, fish, marine and/or microbial oils as source of LC-PUFA.

Lipid Component Level One: Fatty Acid Composition

Herein LA refers to linoleic acid and/or acyl chain (18:2 n6); ALA refers to α-linolenic acid and/or acyl chain (18:3 n3); LC-PUFA refers to long chain polyunsaturated fatty acids and/or acyl chains comprising at least 20 carbon atoms in the fatty acyl chain and with 2 or more unsaturated bonds; DHA refers to docosahexaenoic acid and/or acyl chain (22:6, n3); EPA refers to eicosapentaenoic acid and/or acyl chain (20:5 n3); ARA refers to arachidonic acid and/or acyl chain (20:4 n6); DPA refers to docosapentaenoic acid and/or acyl chain (22:5 n3). PA relates to palmitic acid and/or acyl chains (C16:0). Medium chain fatty acids (MCFA) refer to fatty acids and/or acyl chains with a chain length of 6, 8 or 10 carbon atoms.

LA preferably is present in a sufficient amount in order to promote a healthy growth and development, yet in an amount as low as possible to prevent occurrence of obesity later in life. The composition therefore preferably comprises less than 15 wt. % LA based on total fatty acids, preferably between 5 and 14.5 wt. %, more preferably between 6 and 10 wt. %. Preferably the composition comprises over 5 wt. % LA based on fatty acids. Preferably ALA is present in a sufficient amount to promote a healthy growth and development of the infant. The present composition therefore preferably comprises at least 1.0 wt. % ALA based on total fatty acids. Preferably the composition comprises at least 1.5 wt. % ALA based on total fatty acids, more preferably at least 2.0 wt. %. Preferably the composition comprises less than 10 wt. % ALA, more preferably less than 5.0 wt. % based on total fatty acids. The weight ratio LA/ALA should be well balanced in order to prevent obesity, while at the same time ensuring a normal growth and development. Therefore, the present composition comprises a weight ratio of LA/ALA from 2 to 10, more preferably from 3 to 10, more preferably from 3 to 7, more preferably from 3 to 6, even more preferably from 4 to 5.5, even more preferably from 4 to 5.

Preferably the composition comprises less than 10 wt. % short chain fatty acids based on total fatty acids, preferably less than 5 wt. %, preferably less than 2 wt. %. Short chain fatty acids are fatty acids with an acyl chain of 2 to 5.

Since MCFA contribute to a reduced fat mass later in life when administered to an infant, the present composition preferably comprises at least 3 wt. % MCFA based on total fatty acids, more preferably at least 10 wt. %, even more preferably 15 wt. %. Since MCFA reduces body fat deposition with no preference for central fat mass, and since MFCA does not decrease the number of adipocytes, the present composition advantageously comprises less than 50 wt. % MCFA based on total fatty acids, more preferably less than 30 wt. %, even more preferably less than 20 wt. %.

Preferably the present composition comprises LC-PUFA, more preferably n-3 LC-PUFA, since n-3 LC-PUFA reduce obesity later in life, more preferably central obesity. More preferably, the present composition comprises EPA, DPA and/or DHA, even more preferably DHA. Since a low concentration of DHA, DPA and/or EPA is already effective and normal growth and development are important, the content of n-3 LC-PUFA in the present composition, more preferably DHA, preferably does not exceed 15 wt. % of the total fatty acid content, preferably does not exceed 10 wt. %, even more preferably does not exceed 5 wt. %. Preferably the present composition comprises at least 0.15 wt. %, preferably at least 0.35 wt. %, more preferably at least 0.75 wt. %, n-3 LC-PUFA, more preferably DHA, of the total fatty acid content. In one embodiment, the present composition comprises at least 0.15 wt % n-3 LC-PUFA based on total fatty acids selected from the group consisting of DHA, EPA, and DPA, more preferably DHA.

As the group of n-6 fatty acids, especially arachidonic acid (ARA) and LA as its precursor, counteracts the group of n-3 fatty acids, especially DHA and EPA and ALA as their precursor, the present composition comprises relatively low amounts of ARA. The n-6 LC-PUFA, more preferably ARA, content preferably does not exceed 5 wt. %, more preferably does not exceed 2.0 wt. %, more preferably does not exceed 0.75 wt. %, even more preferably does not exceed 0.5 wt. %, based on total fatty acids. Since ARA is important in infants for optimal functional membranes, especially membranes of neurological tissues, the amount of n-6 LC-PUFA, preferably of ARA, is preferably at least 0.02 wt. % more preferably at least 0.05 wt. %, more preferably at least 0.1 wt. % based on total fatty acids, more preferably at least 0.2 wt. %. The presence of ARA is advantageous in a composition low in LA since it remedies LA deficiency. The presence of preferably low amounts of ARA is beneficial in nutrition to be administered to infants below the age of 6 months, since for these infants the infant formulae is generally the only source of nutrition. Preferably the n-6 LC-PUFA/n-3 LC-PUFA weight ratio, more preferably ARA/DHA weigh ratio is below 3, more preferably 2 or below, even more preferably 1 or below. A low n-6 LC-PUFA/n-3 LC-PUFA, more preferably ARA/DHA, ratio is especially preferred when LA/ALA ratio's are above 5, more preferably above 7, in order to counterbalance. In one embodiment, the present nutritional composition comprises LA and ALA in a ratio LA/ALA above 5 and ARA and DHA in a ratio ARA/DHA below 2. In one embodiment, the present nutritional composition comprises LA and ALA in a ratio LA/ALA of 5 or below 5 and ARA and DHA in a ratio AA/DHA of 2 or above 2. Arachidonic acid may also be abbreviated as AA.

Lipid Component Level Two: Palmitic Acid at Sn-2 Position of Triglyceride

According to the present invention, the composition comprises triglycerides. Triglycerides comprise a glyceride molecule to which, via ester bonds, three fatty acid residues are attached, which may be the same or different, and which are generally chosen from saturated and unsaturated fatty acids containing 6 to 26 carbon atoms, including but not limited to LA, ALA, oleic acid (C18:1), PA and/or stearic acid (C18:0). Such fatty acid triglycerides may differ in the fatty acid residues that are present and/or in the respective position(s) of the fatty acid residues (e.g. in the sn-1, -2 and/or -3 position). The triglycerides used in the present invention for the manufacture of a composition are chosen such that the amount of PA residues that are present in the triglycerides are 10 wt. % or more based on total fatty acid present in the triglycerides, preferably more than 15 wt. %. Preferably the amount of PA residues that are present in the triglycerides are below 30 wt. %, more preferably between 16 and 24%. The triglycerides used in the present invention for the manufacture of a composition are chosen such that of the total PA residues present in the triglyceride at least 30%, preferably at least 35%, more preferably at least 40% are in the sn-2 or beta position of the triglyceride.

The triglyceride of the present invention are commercially available—e.g. from Loders Croklaan under the name Betapol™ and/or can be prepared in a manner known per se, for instance as described in EP 0 698 078 and/or EP 0 758 846. Another suitable source is InFat™ of Enzymotec. In case these lipids are obtained by trans- or interesterification of vegetable triglycerides, these sources are in the context of the present invention regarded as vegetable lipids. Preferably the amount of the triglyceride with increased amount of palmitic acid residues on the sn-2 position of a trygliceride molecule that is comprised in the lipid fraction of the composition that is to be administered according to the present method or use, herebelow also named the final composition, is between 10 and 100 wt. %, preferably between 20 and 100 wt. %, more preferably between 20 and 80 wt. %, even more preferably between 50 and 80 wt. %.

A preferred source for triglycerides having palmitic acid at the sn-2 or beta position of the triglyceride is non human animal fat, more preferably non human mammalian milk fat, even more preferably cow's milk fat. Preferably non human mammalian milk fat, in particular cow's milk fat, is used in the form of anhydrous milk fat or butter oil. Preferably the source of the milk fat is in a homogenous fat phase, such as butter oil or anhydrous milk fat, and not in the form of oil in water emulsion such as cream, since the lipid globules of the present invention can be more easily prepared during the manufacture of the nutritional composition of the present invention when in a homogenous fat phase. Preferably the amount of milk fat is between 10 and 100 wt. % based on total lipid, preferably between 10 and 80 wt. % based on total lipid, more preferably between 20 and 80 wt. %, more preferably between 20 and 50 wt. %, even more preferably between 25 and 50 wt. % based on total lipid.

Preferably the amount of the triglyceride with increased amount of palmitic acid residues on the sn-2 position is such that the lipid fraction of the final nutritional composition comprises at least 10 wt. %, more preferably at least 15 wt. % of palmitic acid residues based on total fatty acid residues, and comprise at least 15 wt. % of the palmitic acid residues based on total palmitic acid residues in the sn-2 position of the triglyceride, more preferably at least 25 wt. %, more preferably at least 30 wt. %, even more preferably at least 35 wt. %. Thus preferably at least 25 wt. %, more preferably at least 30 wt. %, even more preferably at least 35 wt. % of the palmitic acid is esterified to the sn-2 position of a triglyceride based on total palmitic acid. Preferably the palmitic acid residues in the final nutritional composition are below 30 wt. % based on total fatty acids comprised in the lipid fraction.

Reduced obesity and/or improved body composition later in life was observed when such lipid component with increased amounts of palmitic acid located at the sn-2 position of triglyceride molecules was consumed early in life.

Lipid Component Level Three: Lipid Globule Design

According to the present invention, lipid is present in the composition in the form of lipid globules. When in liquid form these lipid globules are emulsified in the aqueous phase. Alternatively the lipid globules are present in a powder and the powder is suitable for reconstitution with water or another food grade aqueous phase. The lipid globules comprise a core and a surface. The core preferably comprises vegetable fat and preferably comprises at least 90 wt. % triglycerides and more preferably essentially consists of triglycerides. Not all vegetable lipids that are present in the composition need necessarily be comprised in the core of lipid globules, but preferably a major part is, preferably more than 50% wt. %, more preferably more than 70 wt. %, even more preferably more than 85 wt. %, even more preferably more than 95 wt. %, most preferably more than 98 wt. % of the vegetable lipids that are present in the composition are comprised in the core of lipid globules. In one embodiment the core of the lipid globules comprises at least 40 wt. % triglycerides of vegetable origin, more preferably at least 50 wt %, even more preferably at least 70 wt. % triglycerides of vegetable origin, more preferably the core of the lipid globules comprises at least 85 wt. %, more preferably at least 95 wt. % triglycerides of vegetable origin.

Coating with Phospholipids

The present invention comprises polar lipids. Polar lipids are amphipathic of nature and include glycerophospholipids, glycosphingolipids, sphingomyelin and/or cholesterol. In particular the composition comprises phospholipids (the sum of glycerophospholipids and sphingomyelin). Polar lipids in the present invention relate to the sum of glycerophospholipids, glycosphingolipids, sphingomyelin and cholesterol. Polar lipids, more preferably phospholipids, are present as a coating on the surface of the lipid globule. By 'coating' is meant that the outer surface layer of the lipid globule comprises polar lipids, whereas these polar lipids are virtually absent in the core of the lipid globule. The presence of polar lipids, in particular, phospholipids as a coating or outer layer of the lipid globule in the diet administered early in life was found to advantageously further decrease fat mass, decrease relative fat mass, i.e. obesity, and/or increase lean body mass later in life. Thus in one embodiment the coating preferably comprises phospholipids and/or polar lipids. Not all phospholipids and/or polar lipids that are present in the composition need necessarily be comprised in the coating, but preferably a major part is. Preferably more than 50 wt. %, more preferably more than 70 wt. %, even more preferably more than 85 wt. %, most preferably more than 95 wt. % of the phospholipids and/or polar lipids that are present in the composition are comprised in the coating of lipid globules.

The present composition preferably comprises glycerophospholipids. Glycerophospholipids are a class of lipids formed from fatty acids esterified at the hydroxyl groups on carbon-1 and carbon-2 of the backbone glycerol moiety and a negatively-charged phosphate group attached to carbon-3 of the glycerol via an ester bond, and optionally a choline group (in case of phosphatidylcholine, PC), a serine group (in case of phosphatidylserine, PS), an ethanolamine group (in case of phosphatidylethanolamine, PE), an inositol group (in case of phosphatidylinositol, PI) or a glycerol group (in case of phosphatidylglycerol, PG) attached to the phosphate group. Lysophospholipids are a class of phospholipids with one fatty acyl chain. Preferably the present composition contains PC, PS, PI and/or PE, more preferably at least PC. The present composition preferably comprises sphingomyelin. Sphingomyelins have a phosphorylcholine or phosphorylethanolamine molecule esterified to the 1-hydroxy group of a ceramide. They are classified as phospholipid as well as sphingolipid, but are not classified as a glycerophospholipid nor as a glycosphingolipid. Preferably the present nutritional composition comprises 0.05 to 10 wt. % sphingomyelin based on total lipid, more preferably 0.1 to 5 wt %, even more preferably 0.2 to 2 wt. %.

The present composition preferably comprises glycosphingolipids. The term glycosphingolipids as in the present invention particularly refers to glycolipids with an amino alcohol sphingosine. The sphingosine backbone is O-linked to a charged headgroup such as ethanolamine, serine or choline backbone. The backbone is also amide linked to a fatty acyl group. Glycosphingolipids are ceramides with one or more sugar residues joined in a β-glycosidic linkage at the 1-hydroxyl position. Preferably the present composition contains gangliosides, more preferably at least one ganglioside selected from the group consisting of GM3 and GD3.

Sphingolipids are in the present invention defined as the sum of sphingomyelin and glycosphingolipids. Phospholipids are in the present invention defined as the sum of sphingomyelin and glycerophospholipids. Preferably the phospholipids are derived from milk lipids. Preferably the weight ratio of phospholipids:glycosphingolipids is from 2:1 to 10:1, more preferably 2:1 to 5:1.

The present composition comprises phospholipids. Preferably the present composition comprises 0.5 to 20 wt. % phospholipids based on total lipid, more preferably 0.5 to 10 wt. %, more preferably 1 to 10 wt. %, even more preferably 2 to 10 wt. % even more preferably 3 to 8 wt. % phospholipids based on total lipid. Preferably the present composition comprises 0.1 to 10 wt. % glycosphingolipids based on total lipid, more preferably 0.5 to 5 wt. %, even more preferably 2 to 4 wt %. Preferably the present composition comprises 0.5 to 10 wt. % (glycosphingolipids plus phospholipids) based on total lipid, more preferably 1.0 to 10 wt. % (glycosphingolipids plus phospholipids) based on total lipid.

The present composition preferably comprises cholesterol. The present composition preferably comprises at least 0.005 wt. % cholesterol based on total lipid, more preferably at least 0.02 wt. %, more preferably at least 0.05 wt. %, even more preferably at least 0.1 wt. %. Preferably the amount of cholesterol does not exceed 10 wt. % based on total lipid, more preferably does not exceed 5 wt. %, even more preferably does not exceed 1 wt. % of total lipid.

Preferably the present composition comprises 0.6 to 25 wt. % polar lipids based on total lipid, wherein the polar lipids are the sum of phospholipids, glycosphingolipids, and cholesterol, more preferably 0.6 to 12 wt. %, more preferably 1 to 10 wt. %, even more preferably 2 to 10 wt %, even more preferably 3.0 to 10 wt. % polar lipids based on total lipid, wherein the polar lipids are the sum of phospholipids, glycosphingolipids, and cholesterol.

Preferred sources for providing the phospholipids, glycosphingolipids and/or cholesterol are egg lipids, milk fat, buttermilk fat and butter serum fat (such as beta serum fat). A preferred source for phospholipids, particularly PC, is soy lecithin and/or sunflower lecithin. The present composition preferably comprises phospholipids derived from mammalian milk. Preferably the present composition comprises phospholipids and glycosphingolipids derived from milk. Preferably also cholesterol is obtained from milk. Preferably the polar lipids, in particular phospholipids, are derived from milk. Polar lipids, in particular phospholipids, derived from milk include the polar lipids, in particular phospholipids, isolated from milk lipid, cream lipid, cream serum lipid, butter serum lipid (beta serum lipid), whey lipid, cheese lipid and/or buttermilk lipid. The buttermilk lipid is typically obtained during the manufacture of buttermilk. The butter serum lipid or beta serum lipid is typically obtained during the manufacture of anhydrous milk fat from butter. Preferably the phospholipids, glycosphingolipids and/or cholesterol are obtained from milk cream. The composition preferably comprises phospholipids, glycosphingolipids and/or cholesterol from milk of cows, mares, sheep, goats, buffaloes, horses and camels. It is most preferred to use a lipid extract isolated from cow's milk. The use of polar lipids from milk fat advantageously comprises the polar lipids from milk fat globule membranes, which are more reminiscent to the situation in human milk. Polar lipids, in particular phospholipids, derived from fat milk advantageously decrease fat mass to a larger extent than polar lipids from other sources. The polar lipids, in particular phospholipids, are located on the surface of the lipid globule, i.e. as a coating or outer layer. It was found that when the polar lipids or phospholipids are present in the coating of the lipid globule they are more effective than when they are dry blended into the powdered product, i.e. present as ingredient as such. A suitable way to determine whether the polar lipids are located on the surface of the lipid globules is laser scanning microscopy. The concomitant use of polar lipids in particular phospholipids, derived from domestic animals milk and triglycerides derived from vegetable lipids therefore enables to manufacture coated lipid globules with a coating more similar to human milk, while at the same time providing an optimal fatty acid profile. Suitable commercially available sources for milk polar lipids are BAEF, SM2, SM3 and SM4 powder of Corman, Salibra of Glanbia, and LacProdan MFGM-10 or PL20 from Arla. Preferably the source of milk polar lipids comprises at least 4 wt. % phospholipids based on total lipid, more preferably 7 to 75 wt. %, most preferably 20 to 70 wt. % phospholipids based on total lipid. Preferably the weight ratio phospholipids to protein is above 0.10, more preferably above 0.20, even more preferably above 0.3. Preferably at least 25 wt. %, more preferably at least 40 wt. %, most preferably at least 75 wt. % of the polar lipids, in particular phospholipids, is derived from milk polar lipids.

Methods for obtaining lipid globules with an increased size and/or coating with phospholipids are disclosed in WO 2010/0027258 and WO 2010/0027259.

It is considered that when the lipid component is designed according to the present invention, by having an optimal fatty acid profile with a linoleic acid to alpha-linolenic acid weight. ratio of 2 to 10 and by having an increased amount of palmitic acid located at the sn-2 position of the triglyceride molecule instead of the sn-1 or sn-3 position, and by having the lipid component organized in lipid globules coated with phospholipids a further improved effect on preventing obesity, preventing insulin resistance, preventing diabetes type 2, preventing metabolic syndrome, preventing osteopenia and/or osteoporosis, or improving body composition later in life is observed. In particular the presence of an increased amount of palmitic acid located at the sn-2 position of the triglyceride molecule instead of the sn-1 or sn-3 enhances, preferably in a synergic manner, the anti-obesity or body composition effects of lipids having an optimal fatty acid profile with a linoleic acid to alpha-linolenic acid wt. ratio of 2 to 10 and having the lipid component organized in lipid globules coated with phospholipids.

Lipid Globule Size

Preferably the lipid globules of the present invention have a volume-weighted mode diameter above 1.0 μm, preferably above 3.0 μm, more preferably 4.0 μm or above, preferably between 1.0 and 10 μm, more preferably between 2.0 and 8.0 μm, even more preferably between 3.0 and 8.0 μm, most preferably between 4.0 μm and 8.0 μm. Preferably in addition the size distribution is in such a way that at least 45 volume %, preferably at least 55 volume %, even more preferably at least 65 volume %, even more preferably at least 75 volume % has a diameter between 2 and 12 μm. More preferably at least 45 volume %, preferably at least 55 volume %, even more preferably at least 65 volume %, even more preferably at least 75 volume % has a diameter between 2 and 10 μm. Even more preferably at least 45 volume %, preferably at least 55 volume %, even more preferably at least 65 volume %, even more preferably at least 75 volume % has a diameter between 4 and 10 μm. Preferably less than 5 volume % of the lipid globules has a diameter above 12 um.

Standard infant formulae or growing up milks have lipid globules with mode diameter below 0.5 μm. It was found that large lipid globules have an improved effect on obesity later in life. The percentage of lipid globules is based on volume of total lipid. The mode diameter relates to the diameter which is the most present based on volume of total lipid, or the peak value in a graphic representation, having on the X—as the diameter and on the Y—as the volume (%).

The volume of the lipid globule and its size distribution can suitably be determined using a particle size analyzer such as a Mastersizer (Malvern Instruments, Malvern, UK), for example by the method described in Michalski et al, 2001, Lait 81: 787-796.

In one embodiment, in the nutritional composition according to the invention the lipid globules are at least partly coated on the surface with phospholipids, the amount of phospholipids present in the nutritional composition being from 0.5 to 20 wt. % phospholipids based on total lipid and have a volume mode diameter of 1.0 μm or above. A combination of coating and large lipid globule size has a further improved effect on preventing obesity later in life, when compared to phospholipid coated lipid globules that are small.

Process

The invention also concerns a process for the manufacture of a nutritional composition according to the invention comprising preparing an aqueous phase comprising protein and digestible carbohydrates and preparing a fat phase comprising lipids, wherein phospholipids are present in the aqueous and/or fat phase, wherein the fatty acid composition of the lipid comprises linoleic acid and alpha-linolenic acid in a weight ratio of 2 to 10, wherein the fatty acid composition of the lipid comprises at least 10 wt. % palmitic acid based on total fatty acids, and at least 15 wt. % of the palmitic acid is esterified to the sn-2 position of a triglyceride based on total palmitic acid, mixing the fat and aqueous phase and homogenizing the mixture of fat and aqueous phase into an oil-in-water emulsion with lipid globules at least partly coated on the surface with phospholipids, the amount of phospholipids present in the nutritional composition being from 0.5 to 20 wt. % phospholipids based on total lipid.

Further, the invention relates to the product, preferably the nutritional composition obtained by the process according to the invention for any of the uses or methods according to the invention.

Nutritional Composition

Digestible Carbohydrates

The composition comprises digestible carbohydrate. The digestible carbohydrate preferably provides 30 to 80% of the total calories of the composition. Preferably the digestible carbohydrate provides 40 to 60% of the total calories. When in liquid form, e.g. as a ready-to-feed liquid, the composition preferably comprises 3.0 to 30 g digestible carbohydrate per 100 ml, more preferably 6.0 to 20, even more preferably 7.0 to 10.0 g per 100 ml. Based on dry weight the present composition preferably comprises 20 to 80 wt. %, more preferably 40 to 65 wt. % digestible carbohydrates.

Preferred digestible carbohydrate sources are lactose, glucose, sucrose, fructose, galactose, maltose, starch and maltodextrin. Lactose is the main digestible carbohydrate present in human milk. Lactose advantageously has a low glycemic index. The present composition preferably comprises lactose. The present composition preferably comprises digestible carbohydrate, wherein at least 35 wt. %, more preferably at least 50 wt. %, more preferably at least 75 wt. %, even more preferably at least 90 wt. %, most preferably at least 95 wt. % of the digestible carbohydrate is lactose. Based on dry weight the present composition preferably comprises at least 25 wt. % lactose, preferably at least 40 wt. %.

Non Digestible Carbohydrates

In one embodiment the present composition comprises non-digestible oligosaccharides. Preferably the present composition comprises non-digestible oligosaccharides with a degree of polymerization (DP) between 2 and 250, more preferably 3 and 60. The non-digestible oligosaccharides advantageously prevent the onset of insulin resistance.

Preferably the present composition comprises fructo-oligosaccharides, galacto-oligosaccharides and/or galacturonic acid oligosaccharides, more preferably galacto-oligosaccharides, most preferably transgalacto-oligosaccharides. In a preferred embodiment the composition comprises a mixture of transgalacto-oligosaccharides and fructo-oligosaccharides. Suitable non-digestible oligosaccharides are for example Vivinal GOS (Frieslandcampina DOMO), Raftilin HP or Raftilose (Orafti).

Preferably, the composition comprises of 80 mg to 2 g non-digestible oligosaccharides per 100 ml, more preferably 150 mg to 1.50 g, even more preferably 300 mg to 1 g per 100 ml. Based on dry weight, the composition preferably comprises 0.25 wt. % to 20 wt. %, more preferably 0.5 wt. % to 10 wt. %, even more preferably 1.5 wt. % to 7.5 wt. %. A lower amount of non-digestible oligosaccharides will be less effective in preventing obesity, whereas a too high amount will result in side-effects of bloating and abdominal discomfort.

Protein

The present composition comprises proteins. The protein component preferably provides 5 to 15% of the total calories. Preferably the present composition comprises a protein component that provides 6 to 12% of the total calories. More preferably protein is present in the composition below 9% based on calories, more preferably the composition comprises between 7.2 and 8.0% protein based on total calories, even more preferably between 7.3 and 7.7% based on total calories. A low protein concentration advantageously ensures a lower insulin response, thereby preventing proliferation of adipocytes in infants. Human milk comprises a lower amount of protein based on total calories than cow's milk. The protein concentration in a nutritional composition is determined by the sum of protein, peptides and free amino acids. Based on dry weight the composition preferably comprises less than 12 wt. % protein, more preferably between 9.6 to 12 wt. %, even more preferably 10 to 11 wt. %. Based on a ready-to-drink liquid product the composition preferably comprises less than 1.5 g protein per 100 ml, more preferably between 1.2 and 1.5 g, even more preferably between 1.25 and 1.35 g.

The source of the protein should be selected in such a way that the minimum requirements for essential amino acid content are met and satisfactory growth is ensured. Hence protein sources based on cows' milk proteins such as whey, casein and mixtures thereof and proteins based on soy, potato or pea are preferred. In case whey proteins are used, the protein source is preferably based on acid whey or sweet whey, whey protein isolate or mixtures thereof and may include α-lactalbumin and β-lactoglobulin. More preferably, the protein source is based on acid whey or sweet whey from which caseino-glyco-macropeptide (CGMP) has been removed. Preferably the composition comprises at least 3 wt. % casein based on dry weight. Preferably the casein is intact and/or non-hydrolyzed. For the present invention protein includes peptides and free amino acids.

Other

The present composition is preferably particularly suitable for providing the daily nutritional requirements to a human with an age below 36 months, particularly an infant with the age below 24 months, even more preferably an infant with the age below 18 months, most preferably below 12 months of age. Hence, the nutritional composition is for feeding or is used for feeding a human subject. The present composition comprises lipid, and protein and digestible carbohydrate wherein the lipid preferably provides 30 to 60% of total calories, the protein preferably provides 5 to 20%, more preferably 5 to 15 wt. %, of the total calories and the digestible carbohydrate preferably provides 25 to 75% of the total calories. Preferably the present composition comprises lipid providing 35 to 50% of the total calories, protein providing 6 to 12% of the total calories and digestible carbohydrate providing 40 to 60% of the total calories. In one embodiment, the protein provides 5 to 9% of the total calories. The amount of total calories is determined by the sum of calories derived from protein, lipids and digestible carbohydrates.

The present composition is not human breast milk. The present composition is not (raw) cow's or other (raw)

mammalian milk. The present composition preferably comprises vegetable lipids. The composition of the invention preferably comprises other ingredients, such as vitamins, minerals according to international directives for infant formulae.

In one embodiment, the nutritional composition according to the invention or the nutritional composition for use according to the invention is a preterm formula, infant formula, follow on formula or growing up milk.

In order to meet the caloric requirements of the infant, the composition preferably comprises 50 to 200 kcal/100 ml liquid, more preferably 60 to 90 kcal/100 ml liquid, even more preferably 60 to 75 kcal/100 ml liquid. This caloric density ensures an optimal ratio between water and calorie consumption. The osmolarity of the present composition is preferably between 150 and 420 mOsmol/l, more preferably 260 to 320 mOsmol/l. The low osmolarity aims to reduce the gastrointestinal stress. Stress can induce adipocyte formation.

Preferably the composition is in a liquid form, with a viscosity below 35 mPa·s, more preferably below 6 mPa·s as measured in a Brookfield viscometer at 20° C. at a shear rate of 100 s$^{-1}$. In one embodiment, the present composition is a powder. Suitably, the composition is in a powdered form, which can be reconstituted with water or other food grade aqueous liquid, to form a liquid, or in a liquid concentrate form that should be diluted with water. It was found that lipid globules maintained their size and coating when reconstituted. When the composition is in a liquid form, the preferred volume administered on a daily basis is in the range of about 80 to 2500 ml, more preferably about 450 to 1000 ml per day.

Infant

Adipocytes proliferate during the first 36 months of life as well as more limited in puberty. The amount of adipocytes is an important determinant in the degree of fat mass, adipose tissue and/or obesity later-in-life. Hence the present composition is preferably administered to the human subject during the first 3 years of life. In one embodiment of the use according to the present invention, the nutritional composition is for feeding a human subject with an age between 0 and 36 months. It was found that there is a predominance of proliferation of adipocytes in the first 12 months of life with an optimum in perinatal adipocyte proliferation. Hence, it is particularly preferred that the present composition is administered to a human subject in this period of life. The present composition is therefore advantageously administered to a human of 0 to 24 months, more preferably to a human of 0 to 18 months, even more preferably to a human of 0 to 12 months, most preferably to a human of 0 to 6 months of age. The present invention particularly aims to prevent obesity later-in-life and is preferably not an obesity treatment. Hence, the present composition is preferably administered to an infant and/or toddler not suffering from obesity or overweight. In one embodiment of the use according to the present invention, the nutritional composition is for feeding a non-obese human subject. Preferably the composition is to be used in infants having a weight appropriate for gestational age.

Although the adipocyte proliferation is most pronounced during the first 36 months of life and puberty, adipocytes are formed also to a lesser degree in the interval between 36 months and puberty. So in one embodiment the present composition is preferably administered to an age up to 5 years, more preferably up to 10 years, more preferably up to 13 years.

Obesity

Obesity in the present invention relates to an excess of body fat mass. Fat mass is also known as adipose tissue or fat tissue. An adult human person suffers from obesity if over 25 wt. % (for man) or over 30 wt. % (for women) of body weight is fat mass. Obesity is sometimes referred to as adiposity.

Suitable ways to determine % body fat mass are underwater weighing, skin fold measurement, bioelectrical impedance analysis, computed tomography (CT/CAT scan), magnetic resonance imaging (MRI/NMR), ultrasonography and dual energy X-ray absorptiometry (DEXA). A preferred method is DEXA measurement. In the context of this invention body fat mass is determined by DEXA.

The increased risk of health problems later in life, such as diabetes, in particular diabetes type 2, and metabolic syndrome, is related to the occurrence of visceral adiposity and not to general obesity. The term 'visceral obesity' refers to a condition with increased visceral fat tissue. Visceral adiposity is typically caused by (accumulation of) excessive visceral fat tissue. Visceral fat, also known as organ fat, intra-abdominal fat, peritoneal fat or central fat, is normally located inside the peritoneal cavity as opposed to subcutaneous fat which is found underneath the skin and intramuscular fat which is found interspersed in skeletal muscles. Visceral fat includes the abdominal fat surrounding the vital organs and includes mesenteric fat, perirenal fat, retroperitoneal fat and preperitoneal fat (fat surrounding the liver). A waist circumference above 102 cm in adult man or above 88 cm in adult women indicates the presence of visceral adiposity. Hip-waist ratio's exceeding 0.9 in man and 0.85 in women indicate visceral adiposity. For children of 3-19 years old appropriate cutoffs for age- and sex-dependent waist circumferences can be found in Taylor et al, 2000 Am J Clin Nutr 72:490-495. A subject suffers from visceral adiposity when it meets one or more of the above criteria (regarding VAT, waist circumference or waist-hip ratio thresholds).

Application

The present composition is preferably administered orally to the infant. The present invention also aims to prevent the occurrence of obesity and/or reduce the fat mass at the age above 36 months. In one embodiment the present method is for preventing obesity, reducing the risk of obesity and/or for improving body composition of a human subject when said human subject has an age above 36 months, preferably when said human subject has an age above 5 years, particularly above 13 years, more particularly above 18 years. In one embodiment the present method or the present nutritional composition is for feeding a human subject with an age between 0 and 36 months and for preventing obesity, reducing the risk of obesity and/or for improving body composition when said human subject has an age above 36 months, preferably to prevent obesity, reduce the risk of obesity and/or improve body composition at the age above 5 years, particularly above 13 years, more particularly above 18 years. In one embodiment the prevention of obesity, reduction of the risk of obesity and/or improving of body composition occurs later in life. With later in life is meant an age exceeding the age at which the diet is taken, preferably exceeding said age with at least one year. In one embodiment the present method or the present nutritional composition is for preventing visceral obesity and/or for reducing the ratio visceral fat to subcutaneous fat. The composition of the present invention therefore advantageously can be used for preventing obesity, reducing the risk of obesity later in life. Likewise the composition can be used to prevent later in life diabetes mellitus type 2, decrease or prevent insulin resistance and/or improve insulin sensitivity, prevent or reduce the risk of metabolic syndrome and prevent or reduce the risk of osteopenia and/or osteoporosis, or reduce the risk of occurrence of osteopenia and/or osteoporosis. Not wishing to be bound by theory a reduced visceral obesity later in life causes these effects. Also improvement of pancreas development and liver function causes these effects.

The inventors surprisingly found that when mice during infancy and childhood were fed a food composition according to the present invention a different and significant effect on body composition later in life was observed compared to mice which during infancy and childhood had been fed a control food composition. Even after consumption of a Western style, mildly obesogenic diet. The composition of the present invention therefore advantageously can be used to improve body composition later in life, in particular increased lean body mass, decreased fat mass, decreased fat mass relative to total body weight, decreased visceral fat mass relative to total body weight, decreased visceral fat mass relative to total fat mass, decreased fat accumulation, increased muscle tissue. The composition of the present invention also advantageously can be used to increase bone mass and increase bone mineral density.

Preterm and/or small for gestational age infants often encounter catch up growth early in life. This is generally seen as a risk factor for later in life adiposity. So the composition of the present invention is advantageously used in preterm infants or small for gestational age (SGA) infants, in particular for feeding a preterm infant or an infant small for gestational age. A preterm or premature infant relates to an infant born before the standard period of pregnancy is completed before or on 37 weeks pregnancy of the mother, i.e. before or on 37 weeks from the beginning of the last menstrual period of the mother. SGA babies are those whose birth weight lies below the 10th percentile for that gestational age. Premature and/or SGA infants include low birth weight infants (LBW infants), very low birth weight infants (VLBW infants), and extremely low birth weight infants (ELBW infants). LBW infants are defined as infants with a weight less than 2500 g. VLBW infants as infants with a weight which is less than 1500 g, and ELBW infants as infants with a weight less than 1000 g.

At a time point corresponding to late adolescence or early adulthood in humans, the mice, which had previously consumed the food composition of the present invention before turning to the Western style diet, had a significantly lower fat mass accumulated and lower percentage fat mass based on body weight and increase muscle tissue than mice which had received a control composition during infancy. The total body weight and lean body mass was increased in the mice fed the experimental diet in early life. In particular visceral obesity was reduced. This is advantageous, since in particular visceral adipose tissue is most associated with health problems.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

EXAMPLES

Example 1

Effects of Structured Lipids on Growth and Body Composition Later in Life

An experiment was performed wherein the effects of an IMF with standard vegetable lipid was compared with IMF wherein the lipid component comprises structured triglycerides with an increased amount of palmitic acid in the sn-2 position.

C57/BL6 dams and their offspring were exposed to the diet from day 2 on. The offspring started eating the diet themselves from day 15 onward. They were completely fed on the diet from day 21 on. The experimental weaning diets were continued until day 42. From day 42 to day 98 all pups were fed the same diet based on AIN-93G diet with an adjusted lipid fraction (containing 10 wt. % lipid of which 50 wt. % lard and 1% cholesterol, based on total lipid), which is representative for a Western style diet.

The experimental diets that were used for weaning were:
1) A rodent diet based on AIN-93G protein, carbohydrates and fibre. Additionally the diet comprised 7 wt. % fat being a mixture of palm oil, coconut oil, rapeseed oil, sunflower oil, and high oleic acid sunflower oil. Typically such vegetable oils comprise only 7.5 wt. % of total palmitic fatty acid residues in the sn-2 position.
2) A rodent diet based on AIN-93G protein, carbohydrates and fibre. Additionally the diet comprised 7 wt. % fat with 30 wt. % based on total fat of a mixture of vegetable oil and 70 wt % based on total fat of Betapol™ 45 (Lipid Nutrition, The Netherlands) wherein about 45% of the total palmitic acid is esterified in the sn-2 position of the triglyceride. The amount of palmitic acid in Betapol™ 45 was about 23 wt. % based on total fatty acid residues.

The triglyceride content in both diets was over 98 wt. % based on total lipids. The fatty acid composition of the diets is given in Table 1 and was very similar.

At day 42, all mice switched to a "Western style diet" comprising 10 wt. % lipid until day 98.

The fatty acid composition of the Western style diet is also shown in Table 1.

TABLE 1

| Fatty acid composition of the diets | | | |
|---|---|---|---|
| | Diet 1, Control | Diet 2, | Western Style diet |
| C12:0 | 11.5 | 11.5 | 5.3 |
| C14:0 | 4.6 | 4.3 | 2.7 |
| C16:0 | 17.1 | 17.1* | 23.1 |
| C18:0 | 3.0 | 2.8 | 9.0 |
| C18:1 n-9 | 36.0 | 38.7 | 40.5 |
| C18:2 n-6 (LA) | 14.0 | 14.0 | 11.9 |
| C18:3 n-3 (ALA) | 2.6 | 2.6 | 1.3 |
| Others | 11.2 | 9.3 | 6.7 |

*about 35-45 wt. % of palmitic acid residues at the sn-2 position of the triglycerides.

The mice were weighed twice a week. The food intake was determined once a week during the entire experiment. To determine body composition (i.e., BMC, BMD, fat mass (FM) and fat-free mass (FFM)) DEXA scans (Dual Energy X-ray Absorbiometry) were performed under general anesthesia at day 42, 70, and 98 days after birth respectively, by densitometry using a PIXImus imager (GE Lunar, Madison, Wis., USA). At the age of 98 days the male mice were sacrificed and fat tissues and organs were weighted.

Interestingly, the mice of both diets showed a different growth pattern during dietary intervention. Based on mean litter weight, and after day 21, mean body weight, the experimental group showed less (but non-significant) weight compared to the control group between day 2 and day 31. From day 37 to day 42 mean body weight of pups fed the experimental diet, started to be higher than the control group.

The results are shown in table 2. On day 42 a direct diet effect of the structured lipid was observed in that body weight, lean body mass and fat mass were increased in the mice consuming the lipid of the present invention.

Interestingly, the increased body weight and lean body mass compared to the control mice was maintained later in life, even when the diet was similar. Also an increased bone mineral content was observed later in life.

Unexpectedly, the increase in fat mass and fat % was much lower and at day 98 a decreased % fat mass was observed compared to control mice. Less fat mass has accumulated during the period the mice were on western style diet, despite a higher body weight. Hence, under the same dietary conditions, a healthier body composition later in life is achieved when it is preceded by an improved growth (affecting lean body mass and fat mass) at the end of infancy, i.e. the body is beneficially imprinted during infancy for a healthier growth later in life. Reduced growth very early in life is generally seen as a risk factor for later adiposity, but with the experimental diet this surprisingly did not seem to be the case.

TABLE 2

Body weight Bone mineral Content, Bone Mass density, Fat mass and relative fat mass.

|  | Day | Diet 1 | Diet 2 |
|---|---|---|---|
| Body weight | 42 | 23.8 (0.55) | 24.7 (0.63) |
|  | 70 | 26.8 (0.72) | 30.3 (0.86)* |
|  | 98 | 28.1 (0.67) | 31.8 (1.49)* |
|  | 98-42 | 4.3 (0.27) | 7.1 (1.5) |
| Lean body mass | 42 | 18.0 (0.81) | 20.7 (0.41) |
|  | 70 | 20.0 (0.33) | 22.7 (0.54)* |
|  | 98 | 21.3 90.48) | 22.9 (0.77)* |
|  | 98-42 | 3.4 90.53) | 2.3 (0.33) |
| Bone mineral content | 42 | 0.410 (0.013) | 0.411 (0.010) |
|  | 70 | 0.504 (0.008) | 0.535 (0.014) |
|  | 98 | 0.557 (0.016) | 0.583 (0.18) |
|  | 98-42 | 0.147 90.011) | 0.178 (0.012) |
| Bone mineral density | 42 | 0.045 (0.001) | 0.046 (0.001) |
|  | 70 | 0.053 (0.001) | 0.054 (0.001) |
|  | 98 | 0.053 (0.001) | 0.055 (0.001) |
|  | 98-42 | 0.008 (0.000) | 0.010 (0.001) |
| Fat mass | 42 | 3.7 (0.22) | 4.3 (0.14) |
|  | 70 | 5.1 (0.22) | 5.9 (0.44) |
|  | 98 | 5.1 (0.23) | 5.4 (0.62) |
|  | 98-42 | 1.4 (0.25) | 1.1 (0.51) |
| % Fat mass | 42 | 17.0 (0.39) | 17.6 (0.57) |
|  | 70 | 20.3 (0.57) | 20.4 (0.91) |
|  | 98 | 19.2 (0.78) | 18.8 (1.33) |
|  | 98-42 | 2.3 (0.57) | 0.9 (0.75) |

TABLE 3

Fat tissue and organ weights.

|  | Diet 1 | Diet 2 |
|---|---|---|
| Epididymal fat g (mean s.e.) | 0.561 (0.036) | 0.660 (0.065) |
| Subcutaneous fat g (mean s.e.) | 0.278 (0.015) | 0.356 (0.039) |
| Peri-renal fat g (mean s.e.) | 0.031 (0.004) | 0.039 (0.007) |
| Retroperitoneal fat g (mean s.e.) | 0.125 (0.016) | 0.182 (0.025) |
| Ratio epi + peri + retro/sub | 2.21 | 2.14 |
| Liver g (mean s.e.) | 1.316 (0.055) | 1.348 (0.178) |
| Pancreas g (mean s.e.) | 0.174 (0.010) | 0.203 (0.019) |
| Brain g (mean s.e.) | 0.428 (0.003) | 0.434 (0.005) |
| Muscle tibialis g (mean s.e.) | 0.042 (0.002) | 0.050 (0.002)* |

*$P < 0.05$

Immediately after the final DEXA measurement on PN day 98, dissection was performed. Organs and white adipose tissue (Epididymal, Peri-renal, Inguinal (Subcutaneous) and retroperitoneal fat) were removed and weighed. Results are shown in table 3. The muscle tissue was significantly higher in mice fed during infancy the diet of the present invention than in control mice.

Example 2

Improved Effect of sn2 Palmitic Acid, and Lipid Globule Design on Growth and Body Composition Later in Life An experiment was performed similar to the one of example 1, wherein the effects of diets with similar amount of fat, but with different fat components with respect amount of palmitic acid on the sn-2 position of the triglyceride molecule and lipid globule design.

C57/BL6 dams and their offspring were exposed to the experimental diets from day 2 on. The offspring started eating the diet themselves from day 15 onward. They were completely fed on the diets from day 21 on. The experimental diets were continued until day 42. From day 42 to day 98 all pups were fed the same diet based on AIN-93G diet with an adjusted lipid fraction (containing 20 wt. % lipid (17 wt % lard, 3 wt % soy oil, 0.1 wt % cholesterol). This diet represents a Western style diet.

The experimental diets comprised 282 g of experimental infant milk formula (IMF). The rest of the diet was AIN-93G protein, carbohydrates and fibre. All lipid present in the diet was derived from the IMF. The total amount of lipid was 7 wt % based on dry weight of the animal diet The experimental IMF, which were present in the different diets, were prepared in a similar way as described in example 1B of WO 2010/0027259. Diet 2 was prepared with high pressure homogenization.

The detailed characteristics of the fat component of the different experimental IMFs used for the different animal diets are shown in Table 4. PA stands for palmitic acid.

The amount of DHA was 0.2 wt. %, and the amount of ARA was 0.36 wt. % in all 6 experimental diets. In the Western style diet the amount of LA was 11.9 wt. %, the amount of ALA was 1.3 wt. %, based on total fatty acids and the ratio LA/ALA was 9.15.

For diet 1 a mixture of palm oil, low erucic acid rape seed oil, coconut oil, high oleic sunflower oil, sunflower oil, with a small amount of soy lecithin, and LC-PUFA premix was used and additionally comprised buttermilk powder as a source of milk derived phospholipids. The amount of vegetable fat in the final experimental IMF was about 95 wt % based on total fat.

For diet 2 a mix of anhydrous milk fat, coconut oil, low erucic acid rape seed oil, sunflower oil, high oleic acid sunflower oil, with a small amount of soy lecithin and LC-PUFA premix was used. The amount of vegetable fat was about 52 wt % based on total fat.

Diet 3 was similar to diet 2, but additionally comprised buttermilk powder as a source of milk derived phospholipids. A little less anhydrous milk fat was added in order to compensate for the milk fat present in butter milk powder. The amount of vegetable fat was about 51 wt % based on total fat.

TABLE 4

Characteristics of the fat component of the experimental diets

|  | Diet 1 | Diet 2 | Diet 3 |
| --- | --- | --- | --- |
| PA* | 18.4 | 18.3 | 17.7 |
| PA at sn-2/total FA wt % | 2.4 | 6.5 | 6.5 |
| PA at Sn-2/total PA | 13 | 35 | 36 |
| LA* | 13.6 | 14.0 | 14.0 |
| ALA* | 2.53 | 2.59 | 2.59 |
| LA/ALA | 5.4 | 5.4 | 5.4 |
| PL** | 1.62 | 0.13 | 1.62 |
| Milk derived PL | 1.49 | 0 | 1.49 |
| Size*** | 3.6 | 0.46 | 5.6 |
| 2-12 μm % # | 60 | <10% | >45% |

*wt % based on total fatty acids
**wt % based on total fat
***volumetric mode diameter in μm.
Volume based percentage of lipid globules having a diameter between 2 and 12 μm The mice were weighed twice a week. The food intake was determined once a week during the entire experiment. To determine body composition (i.e., bone mass content (BMC), bone mineral density (BMD), fat mass (FM) and fat-free mass/lean body mass (LBW)) DEXA scans (Dual Energy X-ray Absorbiometry) were performed under general anesthesia at day 42, and 70 days after birth respectively, by densitometry using a PIXImus imager (GE Lunar, Madison, Wis., USA).

The results are shown in Table 5

TABLE 5

Effects of early in life diets on development of body weight and composition.

|  | Day | Diet 1 | Diet 2 | Diet 3 |
| --- | --- | --- | --- | --- |
| BW g (s.e.) | 42 | 24.11 (0.36) | 24.55 (0.52) | 24.56 (0.21) |
|  | 70 | 29.81 (0.94) | 30.68 (0.90) | 30.24 (0.66) |
| LBM (g (s.e.) | 42 | 19.47 (0.42) | 20.07 (0.56) | 20.02 (0.34) |
|  | 70 | 21.61 (0.51) | 22.73 (0.57) | 22.73 (0.39) |
| Fat g.(s.e) | 42 | 3.72 (0.12) | 3.72 (0.14) | 3.44 (0.12) |
|  | 70 | 7.25 (0.53) | 7.38 (0.66) | 7.04 (0.50) |
| Fat % of body mass | 42 | 15.99 (0.32) | 15.62 (0.40) | 14.70 (0.57) |
|  | 70 | 24.83 (1.13) | 24.11 (1.25) | 23.59 (1.21) |
| BMC g (s.e.) | 42 | 0.38 (0.01) | 0.39 (0.01) | 0.38 (0.01) |
|  | 70 | 0.44 (0.01) | 0.46 (0.01) | 0.47 (0.01) |
| BMD g/cm$^2$ (s.e.) | 42 | 0.0465 (0.0004) | 0.0469 (0.0007) | 0.0473 (0.0006) |
|  | 70 | 0.052 (0.0008) | 0.053 (0.0008) | 0.055 (0.0008) |

As shown in Table 5 a combination of a lipid with an increased amount of palmitic acid at the sn-2 position and a lipid globule increased in size and coated with phospholipids while at the same time having a low LA/ALA ration (diet 3) showed an improved effect on body composition later in life regarding increased lean body mass, decreased fat mass, decreased fat % of body mass, increased bone mineral content and increased bone mineral density, when compared with diet without an increased amount of palmitic acid at the sn-2 position (diet 1) or with a diet with small lipid globules not coated with phospholipids (diet 2). This effect was already present to some extent on day 42, i.e. directly after having consumed the early in life diets. But strikingly the effects were even more pronounced at day 70, when the animals had been fed the same Western style diet for a while.

This is indicative for an improved effect on body composition and prevention of disorders, in particular later in life, such as obesity, metabolic syndrome, diabetes type 2 and osteopenia when consuming a diet comprising lipid with a LA/ALA between 2 to 10, at least 10 wt. % palmitic acid based on total fatty acids with at least 15% of the palmitic acid residues on the sn-2 position, and in the presence of 0.5 wt. % to 20 wt. % based on total fat of phospholipids in the coating of the lipid globules further improved by the lipid globules being increased in size.

Example 3

IMF with Structured Lipids

An infant formula for infants of 0 to 6 months comprising per 100 ml 66 kcal, 1.3 g protein (cow's milk protein, whey protein and casein in a weight ratio of 6:4), 7.3 g digestible carbohydrates (mainly lactose), 3.5 g lipid (mainly vegetable lipids), 0.54 g non-digestible oligosaccharides (trans galacto-oligosaccharides and long chain fructooligosaccharide), minerals, trace elements, vitamins, carnitine, choline, myo-inositol, and taurine as known in the art.

The fatty acid composition is similar as in diet 2 of example 1 except that due to presence of microbial oils 0.2 wt. % n3 LC-PUFA (mainly DHA) and 0.35 wt % AA is present.

Additionally 0.6 wt. % phospholipids from butter milk serum powder was present (source SM2 of Corman, Belgium) based on total lipid. The process was as performed as of Diet 4 in the example 1 of WO 2010/0027258 and the lipid globules had a volume mean diameter above 1.0 μm and had a surface layer comprising phospholipids.

Example 4

Infant Formula

An infant formula comprising per 100 ml 66 kcal, 1.3 g protein (cow's milk derived protein, with whey protein and casein in a weight ratio of 6:4), 7.3 g digestible carbohydrates (mainly lactose), 3.4 g lipid of which 51 wt % vegetable fat (low erucic acid rape seed oil, sunflower oil, coconut oil, high oleic acid sunflower oil, soy lecithin) 48 wt. % milk fat (mainly anhydrous milk fat, and butter milk powder), the remainder being fish oil microbial oil as a source of LC-PUFA, 0.8 g non-digestible oligosaccharides (trans galacto-oligosaccharides and long chain fructo-oligosaccharide). Minerals, trace elements, vitamins, carnitine, choline, myo-inositol, and taurine as known in the art.

Butter milk powder is present in an amount such that 1.5 wt. % phospholipids (derived from butter milk powder) based on total lipid was present. Additionally 0.1 wt % soy derived phospholipid is present based on total fat. The lipid globules had a surface layer comprising at least part of the phospholipids. The lipid globules had a volume mean diameter of about 5 μm.

The fatty acid profile based on total fatty acid comprises 17.70 wt. % PA (of which 36% based on total PA is on the sn-2 position), 13.96 wt. % LA, 2.59 wt. % ALA, 0.36 wt. % ARA, 0.2 wt. % DHA, 0.06 wt. % EPA and 0.03 wt % DPA.

The invention claimed is:

1. A method of prevention of obesity, reducing the risk of obesity, treatment of obesity, prevention of diabetes type 2, reducing the risk of occurrence of insulin resistance and improving insulin sensitivity, preventing metabolic syndrome, comprising administering to a preterm and/or small for gestational age infant a nutritional composition comprising carbohydrates, protein and lipid, wherein the lipid is present in the form of lipid globules comprising:
   (a) linoleic acid and alpha-linolenic acid in a weight ratio of 2 to 10,
   (b) at least 10 wt. % palmitic acid based on total fatty acids, wherein at least 30 wt. % of the palmitic acid is esterified to the sn-2 position of a triglyceride based on total palmitic acid, and
   (c) a surface at least partly coated with phospholipids, wherein the amount of phospholipids present in the nutritional composition being from 0.5 to 20 wt. % phospholipids based on total lipid, and
   wherein the nutritional composition is not human milk.

2. The method of claim 1, wherein the nutritional composition is for feeding a human subject with an age between 0 and 36 months.

3. The method according to claim 2, wherein the prevention, reduction, improvement is observed when the subject is over 36 months.

4. The method according to claim 1, wherein the subject is a non-obese human subject.

5. The method according to claim 1, wherein the composition is a preterm formula, infant formula, follow on formula or growing up milk.

6. The method according to claim 1, wherein the composition comprises less than 15 wt. % linoleic acid and more than 1 wt. % alpha-linolenic acid based on total fatty acids.

7. The method according to claim 1, wherein the composition comprises at least 0.15 wt % n-3 LC-PUFA based on total fatty acids selected from the group consisting of DHA, EPA, and DPA.

8. The method according to claim 1, wherein at least 35 wt. % of the palmitic acid is esterified to the sn-2 position of a triglyceride based on total palmitic acid.

9. The method according to claim 1, wherein the lipid globules have a volume mode diameter of 1.0 μm or above.

10. The method according to claim 1, wherein 0.5 to 20 wt. % of the phospholipids derived from mammalian milk based on total lipid.

11. The method according to claim 1, wherein the composition comprises a core of lipid globules comprising at least 40 wt. % of triglycerides of vegetable origin.

12. The method according to claim 1, wherein the composition comprises 10 to 50 wt. % lipids based on dry weight of the total composition.

13. The method according to claim 1, wherein the lipids provide 30 to 60% of the total calories, the protein provides 5 to 20% of the total calories and the digestible carbohydrates provide 25 to 75% of the total calories.

14. The method according to claim 1, wherein the protein provides 5 to 9% of the total calories.

15. The method according to claim 1, wherein the composition further comprises non digestible oligosaccharides.

16. The method according to claim 1, wherein the composition is a powder.

17. A method of improving body composition, the improvement of body composition being selected from the group consisting of increased lean body mass, decreased fat mass relative to total body weight, decreased visceral fat mass relative to total body weight, a decreased visceral fat mass relative to total fat mass, decreased fat accumulation and increased muscle mass, the method comprising administering to a preterm and/or small for gestational age infant a nutritional composition comprising carbohydrates, protein and lipid, wherein the lipid is present in the form of lipid globules comprising:
   (a) linoleic acid and alpha-linolenic acid in a weight ratio of 2 to 10,
   (b) at least 10 wt. % palmitic acid based on total fatty acids, wherein at least 30 wt. % of the palmitic acid is esterified to the sn-2 position of a triglyceride based on total palmitic acid, and
   (c) a surface at least partly coated with phospholipids, wherein the amount of phospholipids present in the nutritional composition being from 0.5 to 20 wt. % phospholipids based on total lipid, and
   wherein the nutritional composition is not human milk.

* * * * *